United States Patent
Ghosh

(10) Patent No.: US 11,541,381 B1
(45) Date of Patent: Jan. 3, 2023

(54) SOLID-SUPPORTED AMINO-DIPHOSPHINE LIGAND CATALYSTS FOR SELECTIVE OLIGOMERIZATION OF ETHYLENE TO FORM LINEAR ALPHA-OLEFINS

(71) Applicant: Saudi Arabian Oil Company, Dhahran (SA)

(72) Inventor: Yagnaseni Ghosh, Cambridge, MA (US)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 17/405,602

(22) Filed: Aug. 18, 2021

(51) Int. Cl.
*B01J 31/02* (2006.01)
*C07C 2/36* (2006.01)

(52) U.S. Cl.
CPC ............ *B01J 31/0275* (2013.01); *C07C 2/36* (2013.01); *C07C 2531/24* (2013.01)

(58) Field of Classification Search
None
See application file for complete search history.

(56) References Cited

U.S. PATENT DOCUMENTS

| | | | |
|---|---|---|---|
| 8,252,871 B2 | 8/2012 | Aliyev et al. | |
| 9,637,508 B2 | 5/2017 | Lee et al. | |
| 10,407,358 B2 | 9/2019 | Wei et al. | |
| 2011/0172370 A1 | 7/2011 | Aliyev et al. | |

FOREIGN PATENT DOCUMENTS

| | | |
|---|---|---|
| CA | 2629885 | 5/2007 |
| WO | 2018170054 A1 | 9/2018 |

OTHER PUBLICATIONS

Posset et al. "Immobilization of Bisphosphinoamine Linkers on Silica: Identification of Previously Unrecognized Byproducts via 31P CP/MAS and Suspension HR-MAS Studies", Chem. Mater. 2005, 17, 586-595. (Year: 2005).*
Shao et al. "Ethylene oligomerization in zeolite-grafted Cr(III)-diphosphinoamine catalysts using triisobutylaluminium as cocatalyst: Change from dimerization to trimerization due to confinement effect", Applied Catalysis A, General 544 (2017) 154-160; Journal Article. (Year: 2017).*

(Continued)

*Primary Examiner* — Ali Z Fadhel
(74) *Attorney, Agent, or Firm* — Dinsmore & Shohl LLP

(57) ABSTRACT

Ethylene oligomerization catalysts include a solid support having surface hydroxyl groups on a surface of the solid support. Functional groups attached to the solid support through at least one covalent bond and coordinated with at least one catalytically active transition metal. Individual functional groups are attached to the solid support as products of condensation reactions of at least one hydrolysable group of precursor ligands with a corresponding surface group of the solid support. The precursor ligands have a general formula $(Ph_2P)_2N—R^1-A$, where $R^1$ is $C_1$-$C_{40}$ hydrocarbylene or $C_1$-$C_{40}$ heterohydrocarbylene; and A is a hydrolysable group selected from trialkoxysilyl, halosilyl, carboxylates, esters, phosphonates, amines, imines, thiols, thiocarboxylates, or halides.

18 Claims, 2 Drawing Sheets

(56) References Cited

OTHER PUBLICATIONS

Shao et al. "Ethylene oligomerization in zeolite-grafted Cr(III)-diphosphinoamine catalysts using triisobutylaluminium as cocatalyst: Change from dimerization to trimerization due to confinement effect", Applied Catalysis A, General 544 (2017) 154-160; Web version. (Year: 2017).*

Zhang Li et al. "Immobilized nickel(II) on organic-inorganic hybrid materials: The effective and reusable catalysts for Biginelli reaction", Sci China Chem, Jan. 2011 vol. 54 No. 1. (Year: 2011).*

Agapie, "Selective ethylene oligomerization: Recent advances in chromium catalysis and mechanistic investigations", Coordination Chemistry Reviews, vol. 255, pp. 861-880, 2011.

Belov, "Tetramerization of Ethylene to Octene-1 (A Review)", Petroleum Chemistry, vol. 52, No. 3, pp. 139-154, 2012.

Blann et al., "Ethylene tetramerisation: Subtle effects exhibited by N-substituted diphosphinoamine ligands", Journal of Catalysis, vol. 249, pp. 244-249, 2007.

Bollmann et al., "Ethylene Tetramerization: A New Route to Produce 1-Octene in Exceptionally High Selectivities", J. Am Chem. Soc, vol. 126, pp. 14712-14713, 2004.

Elowe et al., "Nitrogen-Linked Diphosphine Ligands with Ethers Attached to Notrogen for Chromium Catalyzed Ethylene Tri- and Tetramerizations", Organometallics, vol. 25, pp. 5255-5260, 2006.

Haag et al., "Effects of Al/Zr ratio on ethylene-propylene copolymerization with supported-zirconocene catalysts", Journal of Molecular Catalys A: Chemical, vol. 169, pp. 275-287, 2001.

Keim, Oligomerization of Ethylene to alpha-Olefins: Discovery and Development of the Shell Higher Olefin Process (SHOP), Angewandte Essays, Angew. Chem. Int. Ed. vol. 52, pp. 12492-12496, 2013.

McKittrick et al., "Toward Single-Site, Immobilized Molecular Catalysts: Site-Isolated Ti Ethylene Polymerization Catalysts Supported on Porous Silica", J. Am. Chem. Soc., vol. 126, pp. 3052-3053, 2004.

Peulecke et al., "Immobilized Chromium Catalyst System for Selective Ethene Trimerization to 1-Hexene with a PNPNH Ligand", Chem Cat Chem, vol. 2, pp. 1079-1081, 2010.

Posset et al., "Immobilization of Bisphosphinoamine Linkers on Silica: Identification of Previously Unrecognized Byproducts via 31P CP/MAS and Suspension HR-MAS Studies", Chem Mater., vol. 17, pp. 586-595, 2005.

Shao et al., "Ethylene oligomerization in zeolite-grafted Cr(III)-diphosphinoamine catalysts using triisobutylaluminum as cocatalyst: Change from dimerization to trimerization due to confinement effect", Applied Catalysis A, General, vol. 544, pp. 154-160, 2017.

Shozi et al., "Heterogenization of Some PNP Ligands for the Oligomerization of Ethylene", S. Afr. J. Chem, vol. 65, pp. 214-222, 2012.

Sydora, "Selective Ethylene Oligomerization", Organometallics, vol. 38, pp. 997-1010, 2019.

Zheng et al., "Fragmentation Behavior of Silica-Supported Metallocene/MAO Catalyst in the Early Stages of Olefin Polymerization", Macromolecules, vol. 38, pp. 4673-4678, 2005.

* cited by examiner

SOLID-SUPPORTED AMINO-DIPHOSPHINE LIGAND CATALYSTS FOR SELECTIVE OLIGOMERIZATION OF ETHYLENE TO FORM LINEAR ALPHA-OLEFINS

TECHNICAL FIELD

The present disclosure relates to oligomerization catalysts and to processes of oligomerizing ethylene with the oligomerization catalysts to form alpha-olefins.

BACKGROUND

Alpha-olefins are widely used in the petrochemical industries. On-demand production of alpha-olefins, such as 1-octene, is a highly sought process for converting ethylene feedstock selectively into various products. Alpha-olefins, including 1-octene, are crucial co-monomers for making valuable products such as linear low-density polyethylene (LLDPE).

There are various catalytic pathways to obtain alpha-olefins from ethylene. However, existing processes lead to a distribution of oligomers of varying molar masses, ranging from low molar mass, such as 1-butene, to higher oligomers, such as 1-decene, and low molecular weight polymer, such as polymer with a molecular weight less than 1000 grams per mole. Selective oligomerization of ethylene can be achieved using early transition-metal containing single-site catalysts, and a majority of such processes have predominantly been able to selectively produce 1-hexene via ethylene trimerization. Selective tetramerization has been more challenging. The most successful tetramerization catalysts have included ligands containing an amino-biphosphine functional group, such as $(Ph)_2P$—$N(R)$—$P(Ph)_2$, where R=alkyl, aryl (or PNP) backbone.

The PNP moiety can coordinate with a chromium-complex, such $CrCl_3$, $Cr(acetylacetonate)_3$ etc. to afford an active catalyst. The catalytic pathway of PNP—Cr complexes proceeds via the formation of metallocycle intermediate, which finally affords the alpha-olefin after concerted beta-hydride elimination and reductive elimination. Even so, homogeneous catalyst systems such as PNP—Cr complexes have persistent drawbacks such as producing polymeric side-products that cause reactor fouling.

SUMMARY

There remain ongoing needs to alleviate problems associated with homogeneous ligands, and to provide catalysts having increased activity and 1-octene/1-hexene selectivity ratio toward on-demand production of 1-octene.

To address the ongoing needs, ethylene oligomerization catalysts are provided that include a solid support having surface hydroxyl groups on a surface of the solid support. Immobilizing catalyst on a solid support, retains the selectivity and reactivity of a homogeneous catalyst but modulates the oligomerization of ethylene on single-sites, thus reducing the uncontrolled growth of polymers as side-products. Essentially, this inhibits reactor fouling. Solid supported catalysts are also recoverable. Functional groups are attached to the solid support through at least one covalent bond and coordinated with at least one catalytically active transition metal. Individual functional groups are attached to the solid support as products of condensation reactions of at least one hydrolysable group of precursor ligands with a corresponding surface group of the solid support. The precursor ligands have formula (I):

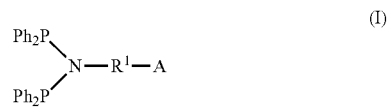

In formula (I), $R^1$ is $C_1$-$C_{40}$ hydrocarbylene or $C_1$-$C_{40}$ heterohydrocarbylene; and A is a hydrolysable group selected from trialkoxysilyl, halosilyl, carboxylates, esters, phosphonates, amines, imines, thiols, thiocarboxylates, or halides.

Additional features and advantages of the embodiments described herein will be set forth in the detailed description that follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
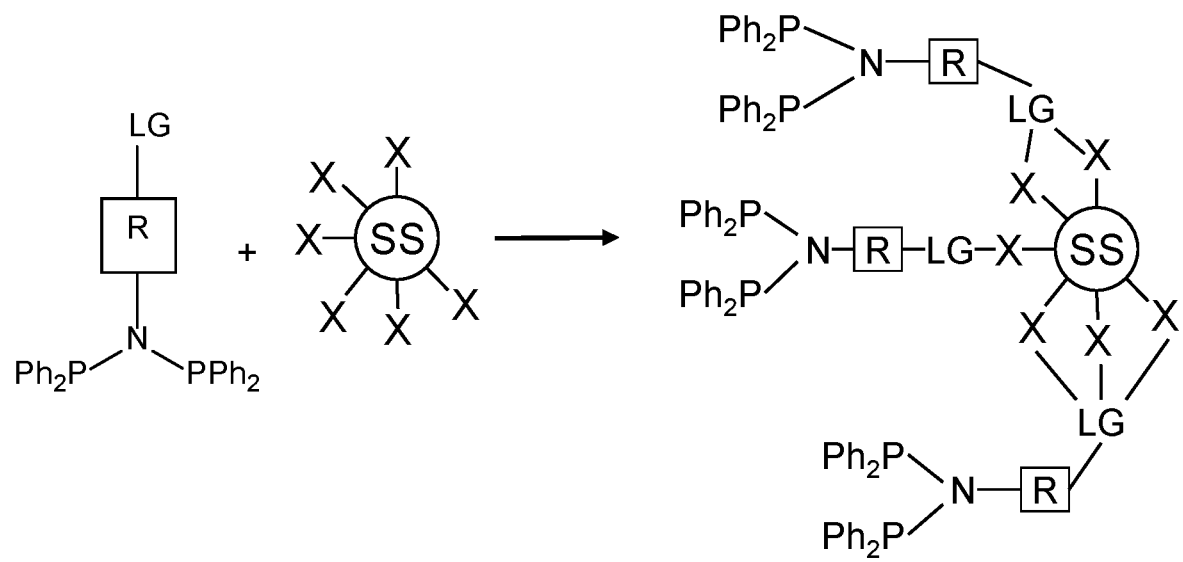
FIG. 1 is a schematic illustration of a preparation of ethylene oligomerization catalysts of this disclosure.

The term "independently selected" is used herein with respect to variable chemical groups to indicate that the variable groups may be identical or different, without regard to the identity of any other variable group.

When used to describe certain carbon atom-containing chemical groups, a parenthetical expression having the form "$(C_x$-$C_y)$" means that the unsubstituted form of the chemical group has from x carbon atoms to y carbon atoms, inclusive of x and y. For example, a $(C_1$-$C_{50})$ alkyl is an alkyl group having from 1 to 50 carbon atoms in its unsubstituted form. In some embodiments and general structures, certain chemical groups may be substituted by one or more substituents. A substituted chemical group defined using the "$(C_x$-$C_y)$" parenthetical may contain more than y carbon atoms depending on the identity of any substituents. For example, a "($C_1$-$C_{50}$) alkyl substituted with exactly one phenyl (—$C_6H_5$)" may contain from 7 to 56 carbon atoms. Thus, in general when a chemical group defined using the "($C_x$-$C_y$)" parenthetical is substituted by one or more carbon atom-containing substituents, the minimum and maximum total number of carbon atoms of the chemical group is determined by adding to both x and y the combined sum of the number of carbon atoms from all of the carbon atom-containing substituents.

The term "substitution" means that at least one hydrogen atom (—H) bonded to a carbon atom or heteroatom of a corresponding unsubstituted compound or functional group is replaced by a substituent. Substituents may be any chemical functional group or radical that could replace a hydrogen atom bonded to a carbon atom or heteroatom of a corresponding unsubstituted compound.

The term "—H" means a hydrogen or hydrogen radical that is covalently bonded to another atom. "Hydrogen" and "—H" are interchangeable, and unless clearly specified have identical meanings.

Except as noted otherwise, the term "hydrocarbon" includes unsubstituted hydrocarbons and substituted hydrocarbons. Unsubstituted hydrocarbons are compounds consisting of carbon atoms and hydrogen atoms. Substituted hydrocarbons are compounds resulting from replacing at least one hydrogen atom of an unsubstituted hydrocarbon with a substituent atom or chemical group. Hydrocarbons may be straight-chain, or branched, aromatic, non-aromatic, cyclic, acyclic, saturated, or unsaturated.

The term "heterohydrocarbon" means a compound resulting from replacing at least one carbon atom, but fewer than all carbon atoms, of an unsubstituted hydrocarbon or a substituted hydrocarbon with a heteroatom. Non-limiting examples of heteroatoms include oxygen, nitrogen, sulfur, and phosphorus.

The term "hydrocarbyl" means a monovalent radical resulting from removal of any hydrogen atom from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "hydrocarbylene" means a divalent radical resulting from removal of any two hydrogen atoms from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "heterohydrocarbyl" means a monovalent radical resulting from removal of any hydrogen atom from a heterohydrocarbon.

The term "heterohydrocarbylene" means a divalent radical resulting from removal of any two hydrogen atoms from a heterohydrocarbon.

The term "aryl" means a monovalent aromatic hydrocarbon radical, in which the carbon atoms of the aromatic system may be substituted or unsubstituted.

The term "arylene" means a divalent aromatic hydrocarbon radical, in which the carbon atoms of the aromatic system may be substituted or unsubstituted. Non-limiting examples of arylenes include substituted or unsubstituted 1,4-phenylene, substituted or unsubstituted 1,3-phenylene, and substituted or unsubstituted 1,2-phenylene.

The term "alkyl" means a monovalent radical resulting from removal of one hydrogen atom from a saturated hydrocarbon radical that may be straight-chain or branched. Accordingly, the term "($C_1$-$C_{20}$) alkyl" means a saturated straight or branched hydrocarbon radical of from 1 to 20 carbon atoms that is unsubstituted or substituted. Examples of unsubstituted ($C_1$-$C_{20}$) alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{20}$) alkyl include trifluoromethyl and trifluoroethyl.

The term "alkylene" means a divalent saturated hydrocarbon radical that may be straight-chain or branched. Accordingly, the term "($C_1$-$C_{20}$) alkyl" means a saturated straight or branched hydrocarbon radical of from 1 to 20 carbon atoms that is unsubstituted or substituted. Examples of unsubstituted ($C_1$-$C_{20}$) alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{20}$) alkyl include trifluoromethyl and trifluoroethyl.

The term "cycloalkyl" means a saturated cyclic hydrocarbon radical. Accordingly, the term "($C_3$-$C_{20}$) cycloalkyl" means a saturated cyclic hydrocarbon radical of from 3 to 20 carbon atoms that is unsubstituted or substituted. Other cycloalkyl groups (e.g., ($C_x$-$C_y$) cycloalkyl) are defined in an analogous manner as having from x to y carbon atoms and being either unsubstituted or substituted. Non-limiting examples of ($C_3$-$C_{40}$) cycloalkyl include cyclopropyl, cyclobutyl, cyclopentyl, cyclohexyl, cycloheptyl, cyclooctyl, cyclononyl, and cyclodecyl, any of which may be substituted or unsubstituted.

The term "($C_1$-$C_{20}$) alkyl-phenyl" means an alkyl having from 1 to 20 carbon atoms, of which, a phenyl substitution is present at the end of the alkyl chain, if the alkyl chain is straight, or at the end of the longest chain, if the alkyl is branched. Non-limiting examples of ($C_1$-$C_{20}$) alkyl-phenyl include phenylmethyl, 2-phenylethyl, 3-phenylpropyl, and 4-phenylbutyl.

The term "amine" means a compound having the general structure —$NR^1R^2$ where R is independently selected from —H and substituted or unsubstituted, linear or branched hydrocarbyl or heterohydrocarbyl. Amines may be primary amines, secondary amines and tertiary amines. When $R^1$ and $R^2$ are both —H, the amine is a primary amine. When either $R^1$ or $R^2$ but not both are —H, the amine is a secondary amine. When neither $R^1$ nor $R^2$ is —H, the amine is a tertiary amine. The term "alkyl amine" means an amine where either $R^1$ or $R^2$ or both $R^1$ and $R^2$ are alkyl, such as methyl or ethyl, for example.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents, one or more double and/or triple bonds optionally may be present in substituents. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents, if any, or in aromatic rings or heteroaromatic rings, if any.

Ethylene tetramerization catalysts that include ligands containing an amino-biphosphine functional group, such as $(Ph)_2P$—N(R)—$P(Ph)_2$, where R=alkyl, aryl (or PNP) have persistent drawbacks such as high production of polymeric side-products, tendencies for reactor fouling, reduced reactivity, and minimum selectivity for producing 1-octene over 1-hexene.

Embodiments of this disclosure include solid-supported PNP based catalysts that have decreased reactor fouling, increased catalytic reactivity, and increased selectivity for producing 1-octene, compared to homogeneous PNP catalysts. The solid-supported PNP—Cr catalysts of this disclosure inhibit polymer generation, thus keeping reactors clean and ready to use after repeated cycles.

Embodiments of this disclosure include an ethylene oligomerization catalyst. The ethylene oligomerization includes a solid support having surface hydroxyl groups on a surface of the solid support; and functional groups attached to the solid support through at least one covalent bond and coordinated with at least one catalytically active transition metal. The individual functional groups are attached to the solid support as products of condensation reactions of at least one hydrolysable group of precursor ligands with a corresponding surface group of the solid support, the precursor ligands having formula (I):

(I)

In formula (I), $R^1$ is $(C_1$-$C_{40})$hydrocarbylene or $(C_1$-$C_{40})$ heterohydrocarbylene; A is a hydrolysable group selected from trialkoxysilyl, halosilyl, carboxylates, esters, phosphonates, amines, imines, thiols, thiocarboxylates, or halides. In some example embodiments, A is trialkoxysilyl or a halosilyl. In further example embodiments, A is trimethoxysilyl or triethoxysilyl.

In some embodiment, the surface group is a surface hydroxyl group or a surface amine. In one or more embodiments, the surface group is a surface hydroxyl group.

In embodiments of this disclosure, the ethylene oligomerization catalyst has a structure according to formula (II):

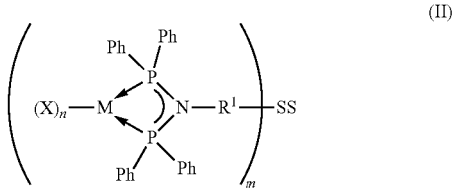

(II)

In formula (II), $R^1$ is $C_1$-$C_{40}$ hydrocarbylene or $C_1$-$C_{40}$ heterohydrocarbylene; SS is a solid support comprising an inorganic oxide; Ph is phenyl; M is a Group VI metal according to IUPAC naming convention; each X comprises a bidentante ligand or a monodentate ligand and is selected from a group consisting of halogen atom or $C_1$-$C_{40}$ heterohydrocarbon; n is 2, 3 or 4; and m is 1 to 100.

In one or more embodiments, the ethylene oligomerization catalyst has a structure according to formula (I) or formula (II), in either of which, the group $R^1$ is a $(C_1$-$C_{40})$ heterohydrocarbylene having one or more groups —N(PPh$_2$).

In one or more embodiments of the ethylene oligomerization catalyst, $R^1$ is a $(C_1$-$C_{40})$heterohydrocarbylene having one or more groups —N(PPh$_2$)—. The phosphorous atom, P, of the group —N(PPh$_2$)— is coordinated to a second metal, M. In one example, $R^1$ may be represented by —$R^2$—N(PPh$_2$)—$R^3$—, where $R^2$ and $R^3$ are $(C_1$-$C_{20})$hydrocarbylene or $(C_1$-$C_{20})$heterohydrocarbylene and $R^2$ includes a coordination to the second metal M. Accordingly, in such embodiments the ethylene oligomerization catalyst has a structure according to formula (III):

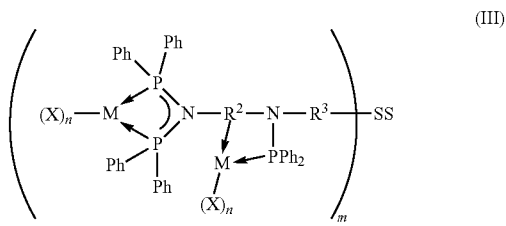

(III)

In formula (III), $R^2$ and $R^3$ are $C_1$-$C_{20}$ hydrocarbylene or $C_1$-$C_{20}$ heterohydrocarbylene; and SS, Ph, m, each M, each X, and each n are as defined in formula (II). It should be apparent that the components $R^2$, $R^3$, and —N(PPh$_2$)— taken together in formula (III) correspond to the group $R^1$ in formula (II).

It should be readily apparent that the ethylene oligomerization catalysts according to formula (III) represent a subset the ethylene oligomerization catalysts according to formula (II). Furthermore, it should be readily apparent that the precursor ligands according to formula (I) may be tethered to a solid support to obtain the ethylene oligomerization catalysts according to formula (II) or formula (III).

In one or more embodiments, the solid support is an inorganic oxide. In some embodiments, the inorganic oxide is silica oxide, alumina oxide or titanium oxide.

In various embodiments of the ethylene oligomerization catalyst, the catalytically active transition metal is chromium. In some embodiments, in formulas (II) and (III), the metal, M, is chromium, molybdenum or tungsten.

In some embodiments, $R^1$ of the ethylene oligomerization catalyst is —$R^2$—N(PPh$_2$)—$R^3$—, in which $R^2$ and $R^3$ are independently $C_1$-$C_{20}$ hydrocarbylene. In various embodiments, $R^1$ is —$R^2$—N(PPh$_2$)—$R^3$—, where $R^2$ and $R^3$ are independently $C_1$-$C_{20}$ alkylene. In one or more embodiments, $R^1$ is 1,4-phenylene or 1,3-phenylene. In other embodiments, $R^1$ is $C_1$-$C_{20}$ alkylene.

The ethylene oligomerization catalysts may include at least one covalent bond that attaches individual functional groups to the solid support and is a bond between a silicon or aluminum atom of the solid support and an oxygen atom of the functional groups.

In the ethylene oligomerization catalyst according to formulas (II) and (III), each X bonds with M through a covalent bond, a dative bond, or an ionic bond. When n is 1, X may be a monodentate ligand or a bidentate ligand; when n is 2, each X is an independently chosen monodentate ligand and may be the same as or different from other groups X. In general, the metal-ligand complex according to formula (I) is overall charge-neutral when in a procatalyst form. In some embodiments, the monodentate ligand may be a monoanionic ligand. Monoanionic ligands have a net formal oxidation state of −1. Each monoanionic ligand may independently be hydride, $(C_1$-$C_{40})$hydrocarbyl carbanion, $(C_1$-$C_{40})$heterohydrocarbyl carbanion, halide, nitrate, carbonate, phosphate, sulfate, HC(O)O$^-$, HC(O)N(H)$^-$, $(C_1$-$C_{40})$hydrocarbylC(O)O$^-$, $(C_1$-$C_{40})$hydrocarbylC(O)N($(C_1$-$C_{20})$hydrocarbyl)$^-$, $(C_1$-$C_{40})$hydrocarbylC(O)N(H)$^-$, $R^KR^LB^-$, $R^KR^LN^-$, $R^KO^-$, $R^KS^-$, $R^KR^LP^-$, or $R^MR^KR^LSi^-$, where each $R^K$, $R^L$, and $R^M$ is independently hydrogen, $(C_1$-$C_{40})$hydrocarbyl, or $(C_1$-$C_{40})$heterohydrocarbyl, or $R^K$ and $R^L$ are taken together to form a $(C_2-C_{40})$hydrocarbylene or $(C_1-C_{20})$heterohydrocarbylene and $R^M$ is hydrogen, $(C_1-C_{40})$hydrocarbyl, or $(C_1-C_{40})$heterohydrocarbyl.

In other embodiments, at least one monodentate ligand X, independently from any other ligands X, may be a neutral ligand. In specific embodiments, the neutral ligand is a neutral Lewis base group such as $R^X NR^K R^L$, $R^K OR^L$, $R^K SR^L$, or $R^X PR^K R^L$, where each $R^X$ independently is hydrogen, $[(C_1-C_{10})hydrocarbyl]_3 Si(C_1-C_{10})hydrocarbyl$, $(C_1-C_{40})$hydrocarbyl, $[(C_1-C_{10})hydrocarbyl]_3 Si$, or $(C_1-C_{40})$heterohydrocarbyl and each $R^K$ and $R^L$ is independently hydrogen, $(C_1-C_{40})$hydrocarbyl, or $(C_1-C_{40})$heterohydrocarbyl.

Additionally, each X can be a monodentate ligand that, independently from any other ligands X, is a halogen, unsubstituted $(C_1-C_{20})$hydrocarbyl, unsubstituted $(C_1-C_{20})$hydrocarbylC(O)O—, or $R^K R^L N$—, wherein each of $R^K$ and $R^L$ independently is an unsubstituted $(C_1-C_{20})$hydrocarbyl. In some embodiments, each monodentate ligand X of the metal-ligand complex is a chlorine atom, $(C_1-C_{10})$hydrocarbyl (e.g., $(C_1-C_6)$alkyl or benzyl), unsubstituted $(C_1-C_{10})$hydrocarbylC(O)O—, or $R^K R^L N$—, wherein each of $R^K$ and $R^L$ independently is an unsubstituted $(C_1-C_{10})$hydrocarbyl and each $R^K$ and $R^L$ is independently hydrogen, $(C_1-C_{40})$hydrocarbyl, or $(C_1-C_{40})$heterohydrocarbyl.

In some embodiments, in the ethylene oligomerization catalyst according to formula (II) or formula (III), subscript n may be 2 or greater than 2, such that there are at least two groups X, and in which any two groups X may be joined to form a bidentate ligand. In illustrative embodiments including a bidentate ligand, the bidentate ligand may be a neutral bidentate ligand. In one embodiment, the neutral bidentate ligand is a diene of formula $(R^D)_2 C=C(R^D)-C(R^D)=C(R^D)_2$, wherein each $R^D$ independently is H, unsubstituted $(C_1-C_6)$alkyl, phenyl, or naphthyl. In some embodiments the bidentate ligand is a monoanionic-mono (Lewis base) ligand. In some embodiments, the bidentate ligand is a dianionic ligand. The dianionic ligand has a net formal oxidation state of −2. In one embodiment, each dianionic ligand independently is carbonate, oxalate (i.e., $^-O_2 CC(O)O^-$), $(C_2-C_{40})$hydrocarbylene dicarbanion, $(C_1-C_{40})$heterohydrocarbylene dicarbanion, phosphate, or sulfate.

In further embodiments, X is selected from methyl; ethyl; 1-propyl; 2-propyl; 1-butyl; 2,2,-dimethylpropyl; trimethylsilylmethyl; phenyl; benzyl; or chloro. In some embodiments n is 2 and each X is identical. In some instances, at least two X are different from each other. In other embodiments, n is 2 and each X is a different one of methyl; ethyl; 1-propyl; 2-propyl; 1-butyl; 2,2,-dimethylpropyl; trimethylsilylmethyl; phenyl; benzyl; and chloro. In one embodiment, n is 2 and at least two X independently are monoanionic monodentate ligands. In some embodiments, n is 2 and the two X groups join to form a bidentate ligand. In other embodiments, the bidentate ligand is 2,2-dimethyl-2-silapropane-1,3-diyl or 1,3-butadiene.

In illustrative embodiments, the ethylene oligomerization catalyst may include individual functional groups attached to the solid support as products of condensation reactions of at least one hydrolysable group of precursor ligands with a corresponding surface group of the solid support, wherein the precursor ligands have any of formulas (1)-(7):

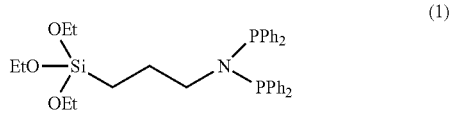
(1)

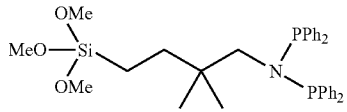
(2)

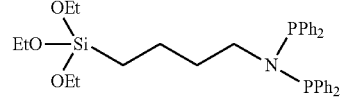
(3)

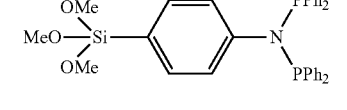
(4)

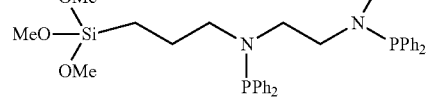
(5)

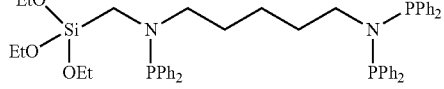
(6)

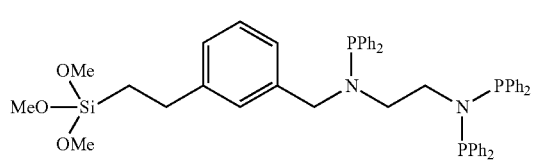
(7)

Cocatalyst Component

The ethylene oligomerization catalysts as previously described may be included as part of a catalyst system for oligomerization of ethylene. The ethylene oligomerization catalyst may be rendered catalytically active by any technique known in the art for activating metal-based catalysts. For example, the ligand coordinated to the metal) optionally may be rendered catalytically active by contacting the complex to, or combining the complex with, an activating co-catalyst.

Examples of activating co-catalysts include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). An example activating technique is bulk electrolysis. Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Examples of polymeric or oligomeric alumoxanes include methylalumoxane, triisobutylaluminum-modified methylalumoxane, and isobutylalumoxane.

The catalyst system that includes the ethylene oligomerization catalysts may be activated to form an active catalyst composition by combination with one or more cocatalysts, for example, a cation forming cocatalyst, a strong Lewis acid, or combinations thereof. Suitable activating co-catalysts include polymeric or oligomeric aluminoxanes, especially methyl aluminoxane, as well as inert, compatible, noncoordinating, ion forming compounds. Exemplary suitable co-catalysts include, but are not limited to modified methyl aluminoxane (MMAO), bis(hydrogenated tallow alkyl)methyl, tetrakis(pentafluorophenyl)borate(1-) amine, and combinations thereof.

Figure 2:
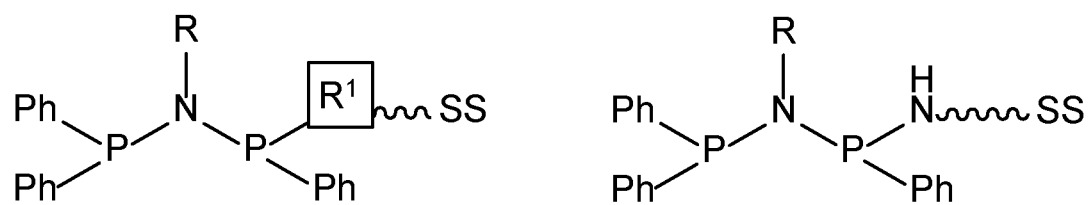
FIG. 2 is a schematic illustration of various ligands according to formula (I) tethered to a solid support (SS) of an ethylene oligomerization catalyst via linking groups (LG) and functional groups (X).
Figure 3:
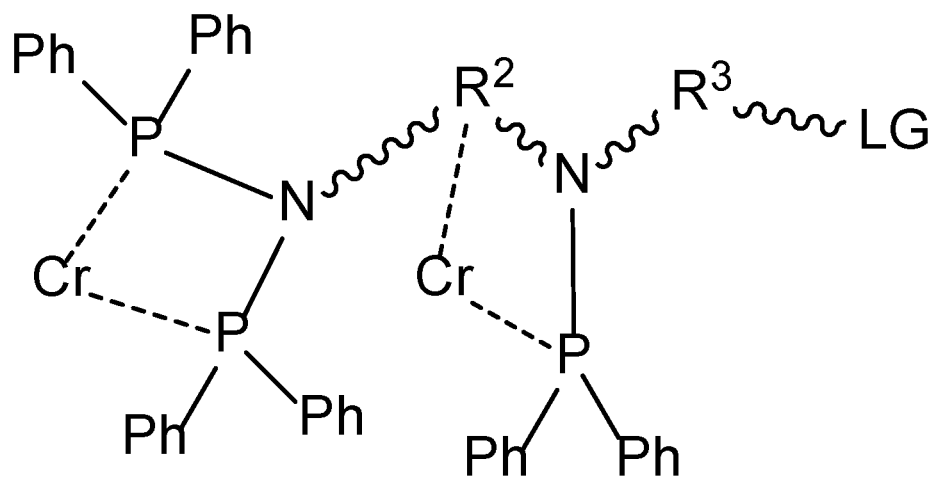
FIG. 3 is an example of an ethylene oligomerization catalyst according to embodiments, in which the ethylene oligomerization catalyst includes a second chromium atom coordinated to the $R^2$ group and the phosphorous atom, and in which LG represents a linking group.
Figure 4:
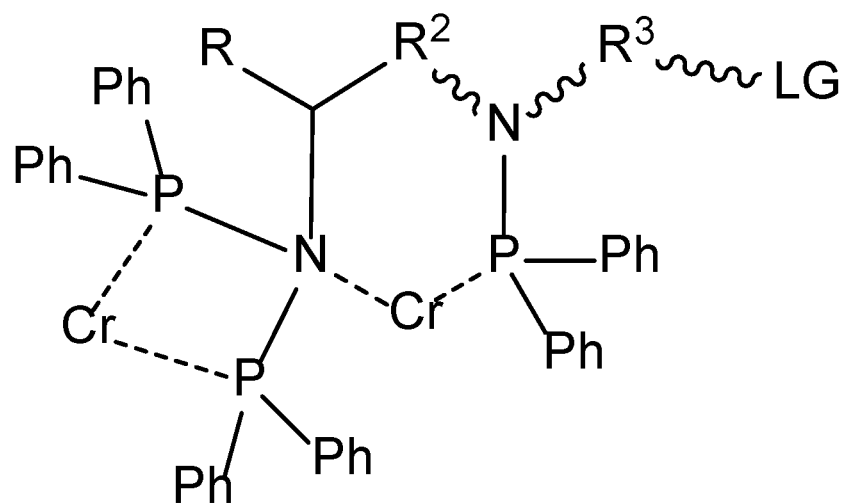
FIG. 4 is an example embodiment of an oligomerization catalyst including a second chromium atom coordinated to the nitrogen atom of a PNP group and the phosphorous atom of a group —$N(PPh_2)$—, and in which LG represents a linking group.

Embodiments of this disclosure include ethylene oligomerization processes incorporating the ethylene oligomerization catalysts. As previously mentioned, the ethylene oligomerization catalysts of this disclosure are tethered via the N atom in a PNP backbone (as illustrated in FIGS. 1-4). Without intent to be bound by theory, tethering via a central N atom in a PNP backbone maintains the complexation geometry of the metal with the PNP, which preserves the steric and electronic effects of the substituents on the central N of PNP. It is believed that electron-withdrawing groups and less bulky groups on the central N atom lead to selectivity toward 1-octene via ethylene tetramerization, while electron donating and sterically bulky substituents on central N lead to 1-hexene via ethylene trimerization.

Embodiments of this disclosure further include methods for oligomerizing ethylene. The methods include contacting ethylene under oligomerization conditions with a catalyst system of one or more ethylene oligomerization catalyst of this disclosure and, optionally, an activator as previously described.

In example embodiments of methods for oligomerizing ethylene, the oligomerization conditions include a reaction temperature from 40° C. to 100° C. and a residence time from 30 minutes to 2 hours. In one or more embodiments, the oligomerization conditions further include a reaction pressure of 14 pounds per square inch (psi) to 500 psi [96.5 kilopascals (kPa) to 3450 kPa].

In various embodiments, the reaction of ethylene with a catalyst system of one or more ethylene oligomerization catalyst of this disclosure under oligomerization conditions is performed in a stirred tank reactor or in a fixed-bed flow reactor.

EXAMPLES

The following examples are offered by way of illustration and in a manner such that one skilled in the art will recognize is not intended to limit the scope of the present disclosure or its claims.

Example 1

General Synthesis

Precursor ligands as described in this disclosure are prepared and tethered to solid supports to obtain catalysts according to the following general synthesis, which is provided as exemplary only. It should be understood that alternative pathways may be possible to prepare the catalysts and that the reactions may be scaled to obtain any desired total yield of catalyst.

All reactants and products are deemed air and moisture-sensitive. Therefore, weighing is performed inside an inert-atmosphere glove box, all solvents and reagents are dry, flushed under nitrogen, or both, and the reaction itself is performed in a Schlenk line under a continuous flow of ultra-pure nitrogen gas.

Reaction 1: Phosphination of trialkoxy silyl amine (R=alkylene)

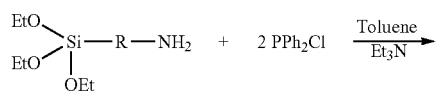

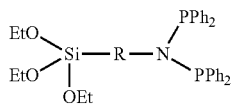

In a 40-mL vial in a glove box and containing a stir-bar, 12 mL of toluene and a requisite volume of trimethylamine (Et$_3$N) are added. A requisite volume of chlorodiphenylphosphine (PPhCl$_2$) is then added dropwise. The solution becomes cloudy and exhibits exothermic evolution of vapors. A 1-mL syringe is loaded with 0.4 mL of omega-aminoalkyltriethoxysilane. The vial is removed from the glove box and is submerged in an acetone/dry-ice bath and stirred under flowing nitrogen. The solution of omega-aminoalkyltriethoxysilane is added dropwise into the solution in the vial. The resulting mixture is stirred for 24 hours then centrifuged at 2500 revolutions per minute (rpm) for 25 minutes. The liquid in the vial is extracted via a 4-inch 16G needle and then transferred to a Schlenk flask via a syringe filter. Solvent is removed via pumping at 80° C. The crude sample is purified by flash chromatography. The precursor ligands are characterized by $^1$H NMR, $^{31}$P NMR, and liquid chromatography mass spectrometry (LC-MS).

Reaction 2: Pre-Treatment of Silica Gel Surface

Excess surface hydroxyl groups can react during catalyst formation with transition metal complexes such as chromium complexes, or with aluminoxane cocatalysts to reduce activity or act poison the catalyst. Therefore, the surface hydroxyl groups are reduced in number, removed, or capped. A silica-gel surface is calcined at 600° C. to 900° C. under vacuum or nitrogen flow to reduce the number of surface hydroxyl groups or to convert the surface hydroxyl groups to terminal groups. The surface hydroxyl groups are converted to unreactive alkoxysilane groups by treatment with trialkoxychlorides.

Reaction 3: Attachment of Precursor Ligand to Inorganic Oxide Support

Approximately 10 mL toluene is added to 250 mg of the pre-treated silica to form a solution that is stirred vigorously inside a glove box. An appropriate amount of the precursor ligand formed by Reaction 1 (approximately 0.1 g to 0.5 g based on the 250 mg of silica in the solution) is weighed, diluted with approximately 1 mL of toluene, and then added dropwise via a pipette into the vigorously stirred suspension of silica in toluene. Stirring is continued overnight inside the glove box. After 8 to 12 hours, the suspension is filtered and washed with toluene. The white precipitate is dried and transferred to vials. The tethered ligands are analyzed by solid-state CP-MAS NMR spectroscopy using the nuclei of $^{31}$P and $^{29}$Si to ascertain the presence of covalent Si—O—Si bonding.

It should be apparent that a similar synthetic approach is applicable to prepare precursor ligands with tethering groups other than the trialkoxysilane by using as a starting material an omega-alkylamine terminated opposite the amine functionality with a group such as a trialkoxysilyl other than triethoxylsilyl, a halosilyl, a carboxylate, an esters, a phosphonate, an amine, an imine, a thiol, a thiocarboxylate, or a halide.

Example 2

Synthesis of Ethylene Oligomerization Catalyst

As a specific example of a precursor ligand and its attachment to a solid support, a precursor ligand was prepared following a procedure analogous to that described in Example 1, with 4-aminobutyltriethoxysilane as the starting reagent.

Step 1: Phosphination of 4-aminobutyltriethoxysilane

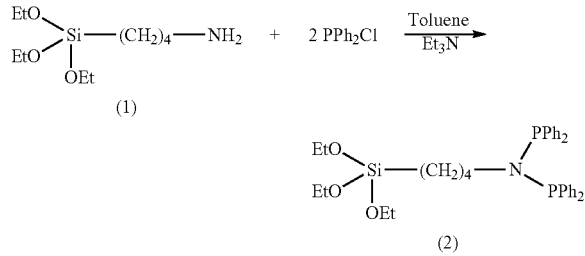

The purified ligand (2) was characterized using $^{31}$P NMR spectroscopy. The disphosphine peak is observed at 62 ppm. A small peak was observed at about 110 ppm corresponding to an oxidation of the phosphine group to yield P=O linkage even after purification. This oxidation is believed to have been caused by use of non-dry solvents during column chromatography.

Step 2: Attachment of 4-N,N-diphosphinoaminobutyltriethoxysilane (2) to silica solid support

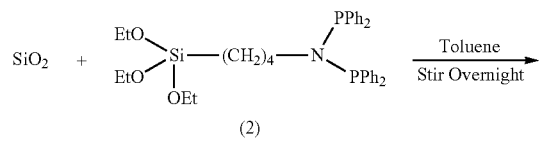

Attachment of the ligand to silica was verified using solid state continuous pulse-magic angle spinning (CP-MAS) NMR spectroscopy. Phosphorus NMR ($^{31}$P) and silicon NMR ($^{29}$Si) were consistent with attachment of the ligand to a silica terminal hydroxy group via a covalent bond.

$^{31}$P solid-state NMR shows the presence of a lone peak at 65 ppm indicating the aminodiphosphine linkage.

$^{29}$Si solid-state NMR exhibited peaks at −50 ppm and −103 ppm, indicating the tertiary (Tn) and quarternary (Qn) Si—O—Si covalent bonds formed between the ligand and silica. The broad peaks Tn and Qn peaks were deconvoluted to show presence of T2 and T3 in Tn and Q3 and Q4 peaks in Qn regions.

The ligand loading on silica was determined by calculating the weight percent content of nitrogen and phosphorus by elemental analysis. The sample prepared according to the present Example 2 was found to contain 0.82% by weight phosphorus, corresponding to 0.26 millimoles phosphorus per gram of silica. The same sample was found to contain less than 0.5% by weight nitrogen.

Example 3

Synthesis of the Ethylene Oligomerization Catalyst

Example 3 provides another specific example of a precursor ligand and its attachment to a solid support. A precursor ligand was prepared following a procedure analogous to that described in Example 1, with N-(6-aminohexyl)aminomethyltriethoxysilane as the starting reagent.

Step 1: Phosphination of N-(6-aminohexyl)aminomethyltriethoxysilane (3)

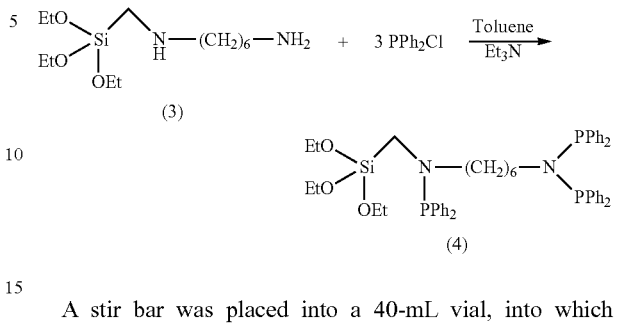

A stir bar was placed into a 40-mL vial, into which approximately 12 mL of dry toluene was added. The N-(6-aminohexyl)aminomethyltriethoxysilane (3) and an additional 12 mL of dry toluene were added, and the resulting mixture stirred at 1000 rpm. Then, dry distilled triethylamine was added to the stirring reaction system. The vial was removed from the glove box and was attached to the Schlenk line to ensure a steady flow of nitrogen gas into the system. The vial was submerged in a dry-ice and acetone bath. When the bath temperature reached about −40° C., the required volume of chlorodiphenylphosphine was added dropwise into the reaction system using a syringe pump. The reaction was stirred overnight on the Schlenk line. After 10 to 12 hours, the vial was placed back in the glove box and was filtered. Solvent was removed, and the resulting crude product was purified by flash chromatography with a 1:1 (v/v) hexane:ethylacetate eluent mixture.

The obtained compound N,N-(6-bis(diphenylphosphino)aminohexyl)-aminomethyl-triethoxysilane (4) was characterized by $^{31}$P NMR spectroscopy. The sample was dissolved in CDCl$_3$ and analyzed with a 400 MHz MBraun NMR spectrometer. A diphosphine peak was present at 67 ppm, and a monophosphine peak was present at 62 ppm.

Reaction 2: Attachment of Ligand Precursor (4) to Silica Solid Support

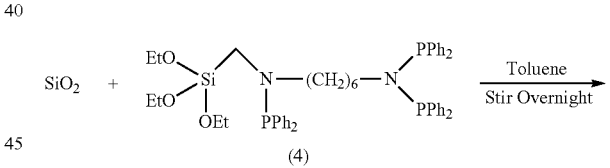

The following reactions were carried out inside an inert atmosphere glove box. Silica gel was dried thoroughly in a furnace operated at 800° C. and then vacuum dried again using Schlenk line. This treatment ensured that excess terminal hydroxyl groups on the silica gel were removed and that any remaining hydroxyl groups were available to form Si—O—Si covalent bonds with the terminal alkoxysilane groups of the ligand precursor (4). Approximately 500 mg of dried silica was weighed into a 40-mL vial, to which 12 mL toluene was added. Under vigorous stirring, a solution of (4) was added dropwise then stirred for 48 hours. Loading of the ligand precursor was carried out at various concentrations, from 0.5 millimoles (mmol) to 2 mmol of ligand precursor per gram of silica. The reaction was filtered inside the glove box.

Attachment of the ligand precursor (4) to the silica solid support was verified by solid state continuous pulse-magic angle spinning (CP-MAS) NMR spectroscopy. The $^{31}$P and $^{29}$Si nuclei NMR were used to prove attachment of ligand to silica via covalent bond formation. The $^{31}$P CP-MAS NMR exhibited a lone peak at 65 ppm corresponding to the aminodiphosphine linkage. The $^{29}$Si solid-state NMR exhibited peaks at −60.77 indicating the tertiary (T‴) Si—O—Si covalent bonds between the ligand and the silica and at −102.54 ppm indicating the quarternary (Q‴) Si—O—Si covalent bonds between the ligand and the silica. Quaternary resonance peaks bunched around −100 ppm indicated the environment of the surface Si atoms on the vacuum dried silica gel. Tertiary resonance peaks indicated the environment around the Si atom on the terminal alkoxysilane group of the catalyst ligand. The combination of both silicon environments was determined to be consistent with the formation of covalent bonds between the ligand precursor (4) and the silica gel.

The ligand loading on the silica was determined by elemental analysis of the sample by calculating the weight contents of nitrogen and phosphorus. The sample prepared according to the present Example 3 was found to contain 1.85% by weight phosphorus, corresponding to 0.60 millimoles phosphorus per gram of silica. The same sample was found to contain 1.19% by weight nitrogen, corresponding to 0.85 millimoles phosphorus per gram of silica.

Example 4

Ethylene Oligomerization Using Solid Supported Catalysts

Ethylene oligomerization catalytic runs are carried out in high-pressure Parr batch reactors (100 mL) and in high throughput micro-scale pressure reactors (8 mL×10 mL).

Solid supported catalysts are premixed with Cr(III) complexes, where coordinating ligands are chloride or acetylacetonate in suitable solvents such as tetrahydrofuran, toluene, methylcyclohexane, fluorobenzene, or chlorobenzene. Ligand to Cr(III) ratios are varied from 1:1 to 1:2 to 2:1.

Activators or catalytic scavengers, depending upon their roles, such as methylaluminoxane (MAO), modified methylaluminoxane (MMAO), silica supported MMAO, triisobutylaluminoxane (TIBAL) are used in the catalytic mixture. The aluminum-to-chromium ratio is varied from 50:1 to 5000:1. The aluminum complexes are mixed with solvents such as toluene or methylcyclohexane.

An internal standard of nonane is used to quantify the amounts of oligomers formed from catalytic runs.

The catalytic runs are carried out in under high pressure of ethylene gas alone and with ethylene and hydrogen gas together. The pressures of gas are varied from 400 psi to 500 psi. The temperatures of the reactions are varied from 40° C. to 60° C. The reactions are run for 30 minutes to 60 minutes.

After the completion of the catalytic runs, the reactions are cooled down and quenched with methanol. Aliquots are taken and analyzed using Gas Chromatography Tandem Mass Spectrometry. The solid products are dried and weighed.

Items Listing

Embodiments of the present disclosure include at least following items, which are not intended to limit the scope of the disclosure as a whole or the appended claims.

Item 1: An ethylene oligomerization catalyst comprising: a solid support having surface hydroxyl groups on a surface of the solid support; and functional groups attached to the solid support through at least one covalent bond and coordinated with at least one catalytically active transition metal; and wherein: individual functional groups are attached to the solid support as products of condensation reactions of at least one hydrolysable group of precursor ligands with a corresponding surface group of the solid support, the precursor ligands having formula (I):

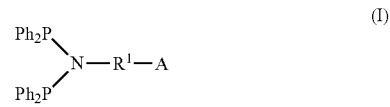

where, in formula (I): $R^1$ is $C_1$-$C_{40}$ hydrocarbylene or $C_1$-$C_{40}$ heterohydrocarbylene; and A is a hydrolysable group selected from trialkoxysilyl, halosilyl, carboxylates, esters, phosphonates, amines, imines, thiols, thiocarboxylates, or halides.

Item 2. The ethylene oligomerization catalyst of Item 1, wherein the solid support is an inorganic oxide.

Item 3. The ethylene oligomerization catalyst of any of Items 1 to 2, wherein the inorganic oxide is silica oxide, alumina oxide, or titanium oxide.

Item 4. The ethylene oligomerization catalyst of any of Items 1 to 3, wherein the surface group is a surface hydroxyl group or amine.

Item 5. The ethylene oligomerization catalyst of any of Items 1 to 4, wherein the catalytically active transition metal is chromium.

Item 6. The ethylene oligomerization catalyst any of Items 1 to 5, wherein $R^1$ is —$R^2$—N(PPh$_2$)—$R^3$—, where $R^2$ and $R^3$ are independently ($C_1$-$C_{20}$)hydrocarbylene or ($C_1$-$C_{20}$) heterohydrocarbylene.

Item 7. The ethylene oligomerization catalyst of any of Items 1 to 6, wherein $R^1$ is —$R^2$—N(PPh$_2$)—$R^3$—, where $R^2$ and $R^3$ are independently ($C_1$-$C_{20}$)alkylene.

Item 8. The ethylene oligomerization catalyst of any of Items 1 to 5, wherein $R^1$ is 1,4-phenylene or 1,3-phenylene.

Item 9. The ethylene oligomerization catalyst of any of Items 1 to 5, wherein $R^1$ is ($C_1$-$C_{20}$)alkylene.

Item 10 The ethylene oligomerization catalyst of any of Items 1 to 9, wherein A is trialkoxysilyl or a halosilyl.

Item 11. The ethylene oligomerization catalyst of any of Items 1 to 9, wherein A is trimethoxysilyl or triethoxysilyl.

Item 12. The ethylene oligomerization catalyst of any of Items 1 to 11, wherein the surface group is a surface hydroxyl group.

Item 13. The ethylene oligomerization catalyst of any of Items 1 to 12, wherein the at least one covalent bond that attaches individual functional groups to the solid support is a bond between a silicon or aluminum atom of the solid support and an oxygen atom of the functional groups.

Item 14. A method for oligomerization of ethylene, the method comprising: contacting ethylene under oligomerization conditions with a catalyst system comprising an ethylene oligomerization catalyst according to any of Items 1 to 13.

Item 15. The method of Item 14, wherein the oligomerization conditions comprise a reaction temperature from 40° C. to 100° C. and a residence time from 30 minutes to 2 hours.

Item 16. The method of any of Items 14 to 15, wherein the oligomerization conditions comprise a reaction pressure of 14 psi to 500 psi.

Item 17. The method of any of Items 14 to 16, wherein the contacting is performed in a stirred tank reactor or in a fixed-bed flow reactor.

Item 18. An ethylene oligomerization catalyst having a structure according to formula (II):

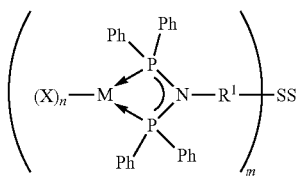

(II)

where, in formula (II): $R^1$ is $C_1$-$C_{40}$ hydrocarbylene or $C_1$-$C_{40}$ heterohydrocarbylene; and SS is a solid support comprising an inorganic oxide; Ph is phenyl; M is a Group VI metal according to IUPAC naming convention; each X comprises a bidentate ligand or a monodentate ligand and is selected from a group consisting of halogen atom or $C_1$-$C_{40}$ heterohydrocarbon; n is 2, 3 or 4; and m is 1 to 100.

Item 19. The ethylene oligomerization catalyst of Item 18, wherein $R^1$ is a ($C_1$-$C_{40}$)heterohydrocarbylene having one or more groups —N(PPh$_2$)—.

Item 20. The ethylene oligomerization catalyst of Item 18 or 19, wherein: $R^1$ is a ($C_1$-$C_{40}$)heterohydrocarbylene comprising at least one group —N(PPh$_2$)—, in which the phosphorus atom of the at least one group —N(PPh$_2$)— is coordinated to a second Group VI metal M, whereby the ethylene oligomerization catalyst of formula (II) has formula (III):

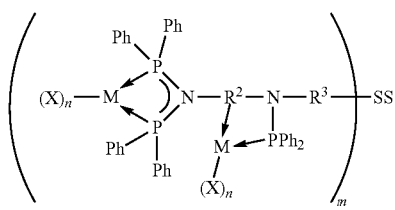

(III)

where, in formula (III): $R^2$ and $R^3$ are ($C_1$-$C_{20}$)hydrocarbylene or ($C_1$-$C_{20}$)heterohydrocarbylene; and SS, Ph, m, each M, each X, and each n are as defined in formula (II).

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

What is claimed is:

1. An ethylene oligomerization catalyst comprising:
   a solid support having surface hydroxyl groups on a surface of the solid support; and
   functional groups attached to the solid support through at least one covalent bond and coordinated with at least one catalytically active transition metal; and wherein:
   individual functional groups are attached to the solid support as products of condensation reactions of at least one hydrolysable group of precursor ligands with a corresponding surface group of the solid support, the precursor ligands having formula (I):

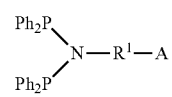

(I)

where:
      $R^1$ is —$R^2$—N(PPh$_2$)—$R^3$—, where $R^2$ and $R^3$ are independently ($C_1$-$C_{20}$)hydrocarbylene or ($C_1$-$C_{20}$)heterohydrocarbylene; and
      A is a hydrolysable group selected from trialkoxysilyl, halosilyl, carboxylates, esters, phosphonates, amines, imines, thiols, thiocarboxylates, or halides.

2. The ethylene oligomerization catalyst of claim 1, wherein the solid support is an inorganic oxide.

3. The ethylene oligomerization catalyst of claim 1, wherein the inorganic oxide is silica oxide, alumina oxide, or titanium oxide.

4. The ethylene oligomerization catalyst of claim 1, wherein the surface group is a surface hydroxyl group or amine.

5. The ethylene oligomerization catalyst of claim 1, wherein the catalytically active transition metal is chromium.

6. The ethylene oligomerization catalyst of claim 1, wherein $R^1$ is —$R^2$—N(PPh$_2$)—$R^3$—, where $R^2$ and $R^3$ are independently ($C_1$-$C_{20}$)alkylene.

7. The ethylene oligomerization catalyst of claim 1, wherein $R^1$ is 1,4-phenylene or 1,3-phenylene.

8. The ethylene oligomerization catalyst of claim 1, wherein $R^1$ is ($C_1$-$C_{20}$)alkylene.

9. The ethylene oligomerization catalyst of claim 1, wherein A is trialkoxysilyl or a halosilyl.

10. The ethylene oligomerization catalyst of claim 1, wherein A is trimethoxysilyl or triethoxysilyl.

11. The ethylene oligomerization catalyst of claim 1, wherein the surface group is a surface hydroxyl group.

12. The ethylene oligomerization catalyst of claim 1, wherein the at least one covalent bond that attaches individual functional groups to the solid support is a bond between a silicon or aluminum atom of the solid support and an oxygen atom of the functional groups.

13. A method for oligomerization of ethylene, the method comprising:
   contacting ethylene under oligomerization conditions with a catalyst system comprising an ethylene oligomerization catalyst according to claim 1.

14. The method of claim 13, wherein the oligomerization conditions comprise a reaction temperature from 40° C. to 100° C. and a residence time from 30 minutes to 2 hours.

15. The method of claim 13, wherein the oligomerization conditions comprise a reaction pressure of 14 psi to 500 psi.

16. The method of claim 13, wherein the contacting is performed in a stirred tank reactor or in a fixed-bed flow reactor.

17. An ethylene oligomerization catalyst having a structure according to formula (II):

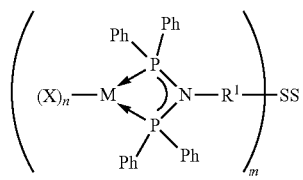 (II)

where:
- $R^1$ is a ($C_1$-$C_{40}$)heterohydrocarbylene having one or more groups —N(PPh$_2$)—; and
- SS is a solid support comprising an inorganic oxide;
- Ph is phenyl;
- M is a Group VI metal according to IUPAC naming convention;
- each X comprises a bidentante ligand or a monodentate ligand and is selected from a group consisting of halogen atom or $C_1$-$C_{40}$ heterohydrocarbon;
- n is 2, 3 or 4; and
- m is 1 to 100.

18. The ethylene oligomerization catalyst of claim 17, wherein:
$R^1$ is a ($C_1$-$C_{40}$)heterohydrocarbylene comprising at least one group —N(PPh$_2$)—, in which the phosphorus atom of the at least one group —N(PPh$_2$)— is coordinated to a second Group VI metal M, whereby the ethylene oligomerization catalyst of formula (II) has formula (III):

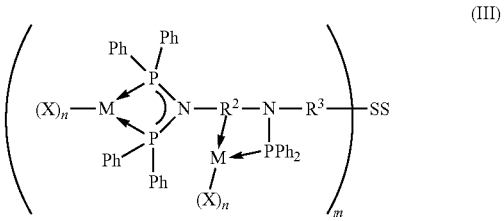 (III)

where:
- $R^2$ and $R^3$ are ($C_1$-$C_{20}$)hydrocarbylene or ($C_1$-$C_{20}$) heterohydrocarbylene; and
- SS, Ph, m, each M, each X, and each n are as defined in formula (II).

\* \* \* \* \*